United States Patent
Wright et al.

(10) Patent No.: US 9,861,420 B2
(45) Date of Patent: *Jan. 9, 2018

(54) FORCE DISSIPATING IMPACTOR DEVICE

(71) Applicant: DePuy Synthes Products, LLC, Raynham, MA (US)

(72) Inventors: Sara R. Wright, West Jefferson, OH (US); Daren L. Deffenbaugh, Winona Lake, IN (US); Edmund W. Frazee, Cromwell, IN (US)

(73) Assignee: DePuy Synthes Products, Inc., Raynham, MA (US)

( * ) Notice: Subject to any disclaimer, the term of this patent is extended or adjusted under 35 U.S.C. 154(b) by 475 days.

This patent is subject to a terminal disclaimer.

(21) Appl. No.: 14/078,808

(22) Filed: Nov. 13, 2013

(65) Prior Publication Data
US 2014/0066942 A1 Mar. 6, 2014

Related U.S. Application Data

(62) Division of application No. 11/526,953, filed on Sep. 26, 2006, now Pat. No. 8,603,099.

(51) Int. Cl.
*A61B 17/56* (2006.01)
*A61B 17/92* (2006.01)
(Continued)

(52) U.S. Cl.
CPC ............ *A61B 17/92* (2013.01); *A61F 2/4637* (2013.01); *A61F 2/40* (2013.01); *A61F 2/4612* (2013.01);
(Continued)

(58) Field of Classification Search
CPC ............... A61B 17/7098; A61B 17/92; A61B 2017/922; A61B 2017/924;
(Continued)

(56) References Cited

U.S. PATENT DOCUMENTS 2,888,258 A * 5/1959 Hoffstrom ............... 267/181
3,438,413 A 4/1969 Borah
(Continued)

FOREIGN PATENT DOCUMENTS

DE 19722923 A1 8/1998
DE 298 17 358 U1 5/1999
(Continued)

OTHER PUBLICATIONS

European Search Report in corresponding European Application (i.e., EP 10 17 8919) dated Mar. 10, 2011 (4 pages).
(Continued)

*Primary Examiner* — Matthew Lawson
(74) *Attorney, Agent, or Firm* — Maginot, Moore & Beck, LLP

(57) ABSTRACT

A force dissipating impactor device comprises a bar member including a hollow shaft, a first end, and a second end. The first end of the impactor device provides an impaction surface and the opposite second end of the impactor device provides an implant engagement surface. The implant engagement surface is contoured to mate with a surface of the implant member. The impaction surface is configured to be struck with a mallet or other tool. A plurality of holes are provided in the shaft and penetrate the surface of the bar member. The plurality of holes provided on the shaft surface of the bar member may be arranged such that a line passing axially along the shaft surface intersects at least one of the plurality of holes. Further, the plurality of holes may be arranged in a staggered matrix around the shaft surface.

16 Claims, 4 Drawing Sheets

(51) Int. Cl.
*A61F 2/40* (2006.01)
*A61F 2/46* (2006.01)
*A61F 2/30* (2006.01)

(52) U.S. Cl.
CPC ............... *A61F 2002/30558* (2013.01); *A61F 2002/30563* (2013.01); *A61F 2002/30784* (2013.01); *A61F 2002/4681* (2013.01); *A61F 2250/0073* (2013.01)

(58) Field of Classification Search
CPC ........ A61B 2017/925; A61B 2017/927; A61B 2017/928; A61F 2/4607; A61F 2/4637; A61F 2002/4642; A61F 2002/4681
USPC .......... 606/91, 99, 100; 623/22.12; 173/210, 173/211; 267/140.3, 181, 182
See application file for complete search history.

(56) References Cited

U.S. PATENT DOCUMENTS

| | | | |
|---|---|---|---|
| 7,931,656 | B2 | 4/2011 | Parry et al. |
| 8,603,099 | B2 * | 12/2013 | Wright et al. ................. 606/99 |
| 2003/0074080 | A1 | 4/2003 | Murray |
| 2003/0083662 | A1 | 5/2003 | Middleton |
| 2003/0229356 | A1 | 12/2003 | Dye |
| 2004/0064145 | A1 | 4/2004 | Ball et al. |
| 2004/0127910 | A1 | 7/2004 | Pubols et al. |
| 2005/0027302 | A1 | 2/2005 | Cueille et al. |
| 2005/0143747 | A1 | 6/2005 | Zubok et al. |
| 2005/0203539 | A1 | 9/2005 | Grimm et al. |

FOREIGN PATENT DOCUMENTS

| | | |
|---|---|---|
| DE | 299 13 088 U1 | 1/2000 |
| EP | 0 549 362 A1 | 6/1993 |
| EP | 0 888 751 A2 | 1/1999 |
| EP | 1 190 687 A1 | 3/2002 |
| EP | 1293179 A1 | 3/2003 |
| EP | 1 405 617 A2 | 4/2004 |
| WO | 00/33750 A1 | 6/2000 |

OTHER PUBLICATIONS

Anatomical Shoulder™Fracture System, Anatomical Shoulder System Meets Fractures © 2005, 2006, Zimmer, Inc. (21 pages).
Anatomical Shoulder™ The New Removable Head Option © 2005, Zimmer, Inc. (6 pages).

* cited by examiner

FORCE DISSIPATING IMPACTOR DEVICE

This is a divisional application of application Ser. No. 11/526,953, filed Sep. 26, 2006, which issued as U.S. Pat. No. 8,603,099 on Dec. 10, 2013, the entire contents of which are herein incorporated by reference.

FIELD

This application relates to the field of impacting devices, such as those used to provide impact force to a prosthetic component in order to secure the prosthetic component to another device or to tissue.

BACKGROUND

Many orthopaedic procedures involve the implantation of prosthetic devices to replace badly damaged or diseased bone tissue. Common orthopaedic procedures that involve prosthetic devices include total or partial hip, knee and shoulder replacement. For example, a hip replacement often involves a prosthetic femoral implant. The femoral implant usually includes a rigid stem that is secured within the natural femur bone tissue. The femoral implant further includes a rounded head that is received by, and may pivot within, a natural or artificial hip socket. Shoulder replacement is somewhat similar, and typically includes a humeral implant that includes a rigid stem and a rounded head. The rigid stem is secured within the natural humerus bone tissue and the rounded head is pivotally received by a shoulder socket.

Increasingly, prosthetic devices are provided as subcomponents that are assembled during surgery. In particular, the different anatomies of different patients require that prosthetic devices such as femoral and humeral implants be available in different sizes and configurations. By way of simplified example, a humeral implant may be available in as many as six or more humeral head diameters. Stems may similarly vary in size and/or in shape. Because of differences in patients and individual conditions, it is advantageous that the surgeon have at her disposal many configurations and sizes of implants. Instead of providing a separate implant for each possible combination of features, implants are provided as modular kits of subcomponents that allow the surgeon to mix and match different subcomponents to achieve the most advantageous combination for the patient. Thus, the surgeon can pick from several sizes or configurations of each component and combine the components to form an implant having an optimal combination of features.

One example of a modular implant is the humeral implant 10 shown in FIGS. 1 and 2. The humeral implant 10 includes a humeral head 12 that may be assembled onto a humeral stem 14. The humeral stem 14 is configured to be implanted in the intramedullary tissue of a natural humeral bone, while the humeral head 12 is configured to be received into the shoulder socket or glenoid cavity.

In the exemplary modular implant of FIGS. 1 and 2, an intermediate component 16 is provided between the humeral head 12 and the humeral stem 14. The intermediate component 16 is a two part insert that includes a stem insert 17 and a head insert 19. The stem insert 17 is provided within a cavity at the end of the stem 14. The head insert 19 includes a truncated ball portion 21 and a frusto-conical portion 23. The truncated ball portion 21 of the head insert is configured to fit within a receptacle in the stem insert 17. The frusto-conical portion 23 serves as a tapered plug 16 that is designed to be received by a tapered receptacle 28 in the humeral head 12. It can be appreciated that the surgeon may secure alternative humeral head 12 designs on the same humeral stem 14, thus providing the surgeon with a broad array of humeral head size options.

Once the components are selected, such as the humeral head 12, the humeral stem 14, and the intermediate component 16 of FIGS. 1 and 2, the components are assembled. One popular method of securing implant components together involves the use of a Morse taper. The components of FIGS. 1 and 2 by way of example include a Morse taper arrangement. In particular, a Morse taper is a feature in which a tapered male component, e.g., the tapered plug 23 of the head insert 19, is received into a tapered female component, e.g., the receptacle 28 of the humeral head 12. The taper angle of the plug 23 is preferably, but need not be, slightly less than the taper angle of the receptacle 28. In use, the plug 23 advances into the receptacle 28, as indicated by arrow 29, until it begins to engage the receptacle 28. The further into the receptacle the plug 23 is forced, the more tightly it engages the humeral head 12.

The force applied to secure the plug 23 within the receptacle 28 is proportional to the retention force of the plug 23 within the receptacle 28. Thus, if a sufficient amount of force is applied, then the humeral head 12 will be securely fastened to the humeral stem 14 via the insert 16. Other prosthetic devices employ Morse tapers for substantially the same reasons.

To apply sufficient force to lock the Morse taper arrangement between the humeral head 12 and the plug 23, it is known to impact the humeral head 12 such that the impact force directs the humeral head 12 toward the plug 23 and humeral stem 14. The impact force drives the plug 23 into the receptacle 18 and forms the Morse taper lock. A hammer or mallet is typically struck directly on the head, or through an impactor device.

During assembly of the implant, the surgeon (or other person) may impact the prosthetic implant several times without knowing if sufficient force has been applied to lock the Morse taper sufficiently. In order to be sure that the Morse taper is locked, the surgeon or assistant may use excessive force. The use of excess force is undesirable because of the potential for damage to the bone tissue or the implant device. For example, the use of excess force may disengage the intermediate components between the head 12 and the stem 14, such as the insert components 17 and 19, from their locked position.

Thus, there is a need for assisting surgical personnel in applying the proper amount of force to a Morse taper to lock the Morse taper. In particular, it would be advantageous to provide an impactor device capable of dissipating the force that is transmitted through the impactor and to an implant when locking a Morse taper. Such an impactor would serve to limit the application of excessive force and any associated damage. The need for such a device is widespread as Morse tapers have commonly been used for connection of many types of implant devices. It would also be advantageous if such an impactor could be manufactured simply and at a low cost.

SUMMARY

A force dissipating impactor device is disclosed herein. The disclosed impactor device is configured to reduce the forces transmitted through the impactor device to an implant. The impactor device comprises a bar member comprising a hollow shaft, a first end, and a second end. The first end of the impactor device provides an impaction surface and the opposite second end of the impactor device provides an implant engagement surface. A plurality of holes are provided in the shaft and penetrate the surface of the bar member.

In one embodiment, the plurality of holes provided on the shaft surface of the bar member are arranged such that a line passing axially along the shaft surface intersects at least one of the plurality of holes. In this embodiment, the plurality of holes may be arranged in a staggered matrix that is provided around the shaft surface. In one embodiment, each row of the staggered matrix comprises four holes, and each hole in a row is situated ninety degrees relative to an adjacent hole in the row.

The implant engagement surface on the first end of the impactor device is contoured to mate with a surface of the implant member. Thus, in one embodiment, the implant engagement surface is rounded and concave and the surface of the implant member is rounded and convex. In one embodiment, the impactor device is between five and nine inches in length, and is preferably about seven inches in length. This length allows the impactor device to be easily handled by the surgeon.

The above described features and advantages, as well as others, will become more readily apparent to those of ordinary skill in the art by reference to the following detailed description and accompanying drawings.

DESCRIPTION

Figure 3:
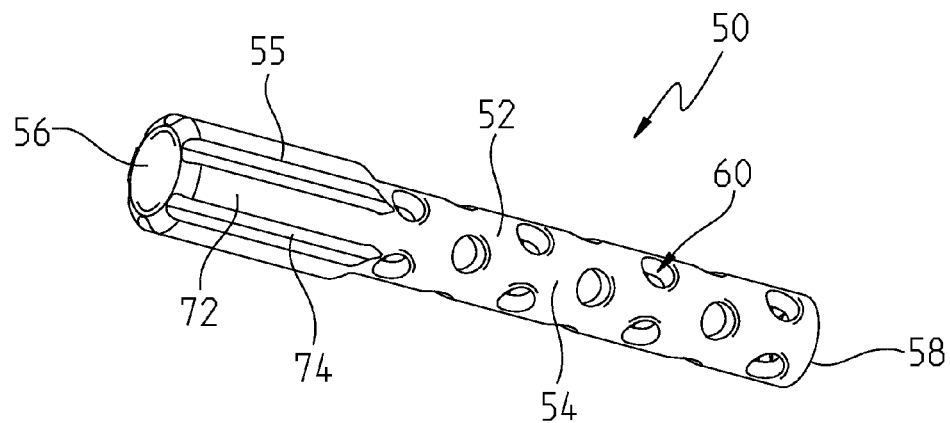
FIG. 3 shows a perspective view of a force dissipating impactor device.
Figure 4:
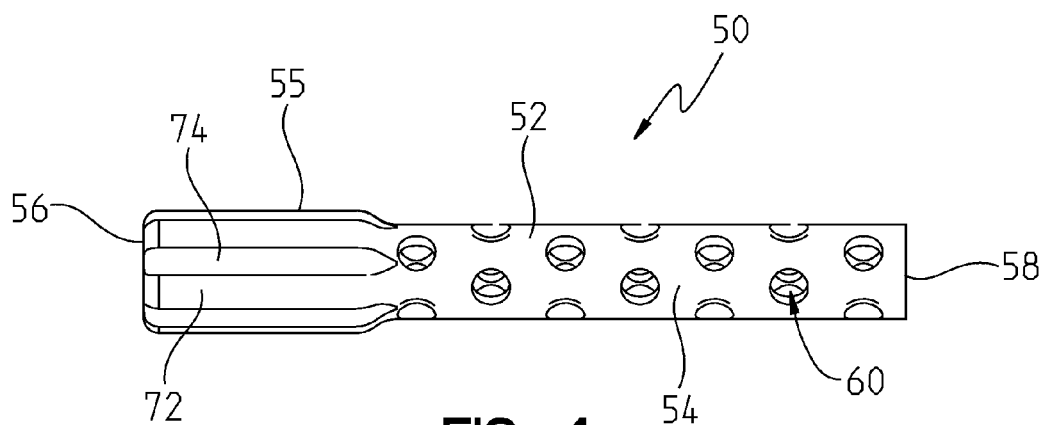
FIG. 4 shows a side view of the impactor device of FIG. 3.
Figure 5:
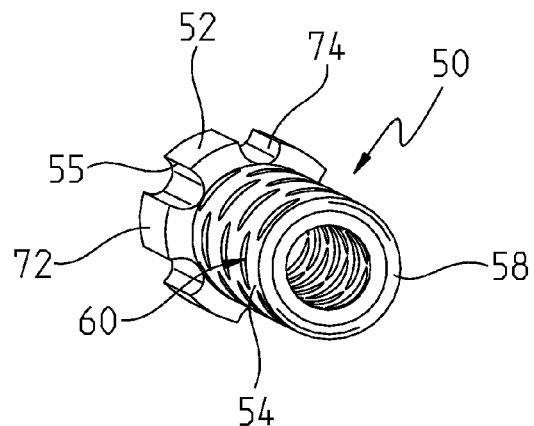
FIG. 5 shows a perspective view of the impactor device of FIG. 3 from an end portion of the impactor device.
Figure 6:
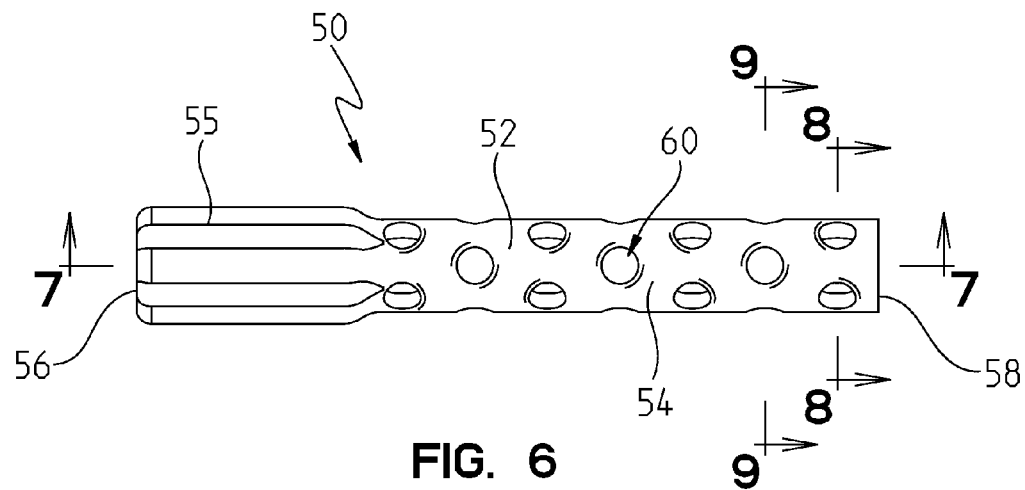
FIG. 6 shows a side view of an alternative embodiment of the impactor device of FIG. 3.
Figure 7:
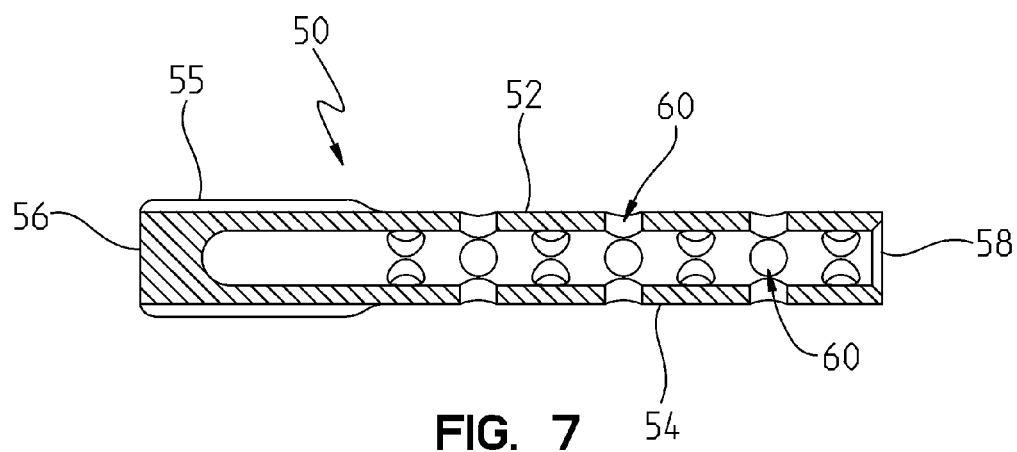
FIG. 7 shows a cross-sectional view of the impactor device along line VII-VII of FIG. 6.

With reference to FIGS. 3-5, an impactor device 50 is disclosed. The impactor device 50 is provided as an elongated bar member 52 that includes a shaft portion 54, a grip 55, a first end 56, and a second end 58. The first end 56 provides an impaction surface and the second end provides a force distributing surface in the form of an implant engagement surface. A plurality of holes 60 are formed in the shaft portion 54.

In the embodiment of FIGS. 3-5, the shaft portion 54 of the impactor device 50 is generally cylindrical in shape. The shaft portion 54 is hollow with a channel 62 extending axially along the center of the shaft portion. The channel 62 is surrounded by an exterior wall 62. Although the exterior wall 62 is cylindrical in the embodiment of FIGS. 3-5, one of skill in the art will recognize that the exterior wall may be any of numerous other shapes, such as box-shaped.

A plurality of holes 60 extend through the exterior wall 62 of the shaft portion 54 and into the axial channel 62, resulting in a perforated shaft portion 54. In the embodiment of FIGS. 3-5, the plurality of holes 60 are arranged on the shaft portion 54 such that any given line passing axially along the surface of the exterior wall will intersect at least one of the plurality of holes 60. To obtain this result, the holes 60 on the shaft portion 54 may be arranged in a staggered matrix around the shaft.

Figure 8:
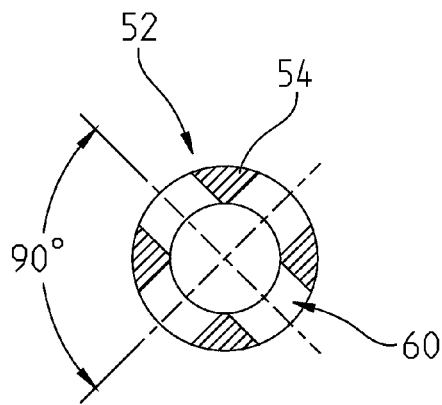
FIG. 8 shows a cross-sectional view of the impactor device along line VIII-VIII of FIG. 6.
Figure 9:
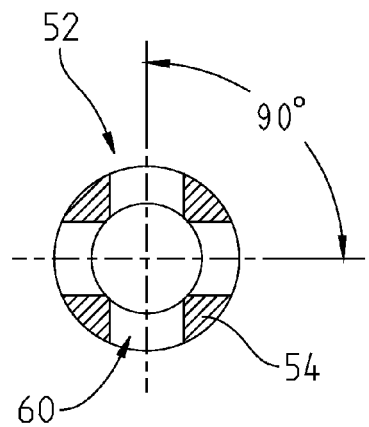
FIG. 9 shows a cross-sectional view of the impactor device along line IX-IX of FIG. 6.
Figure 10:
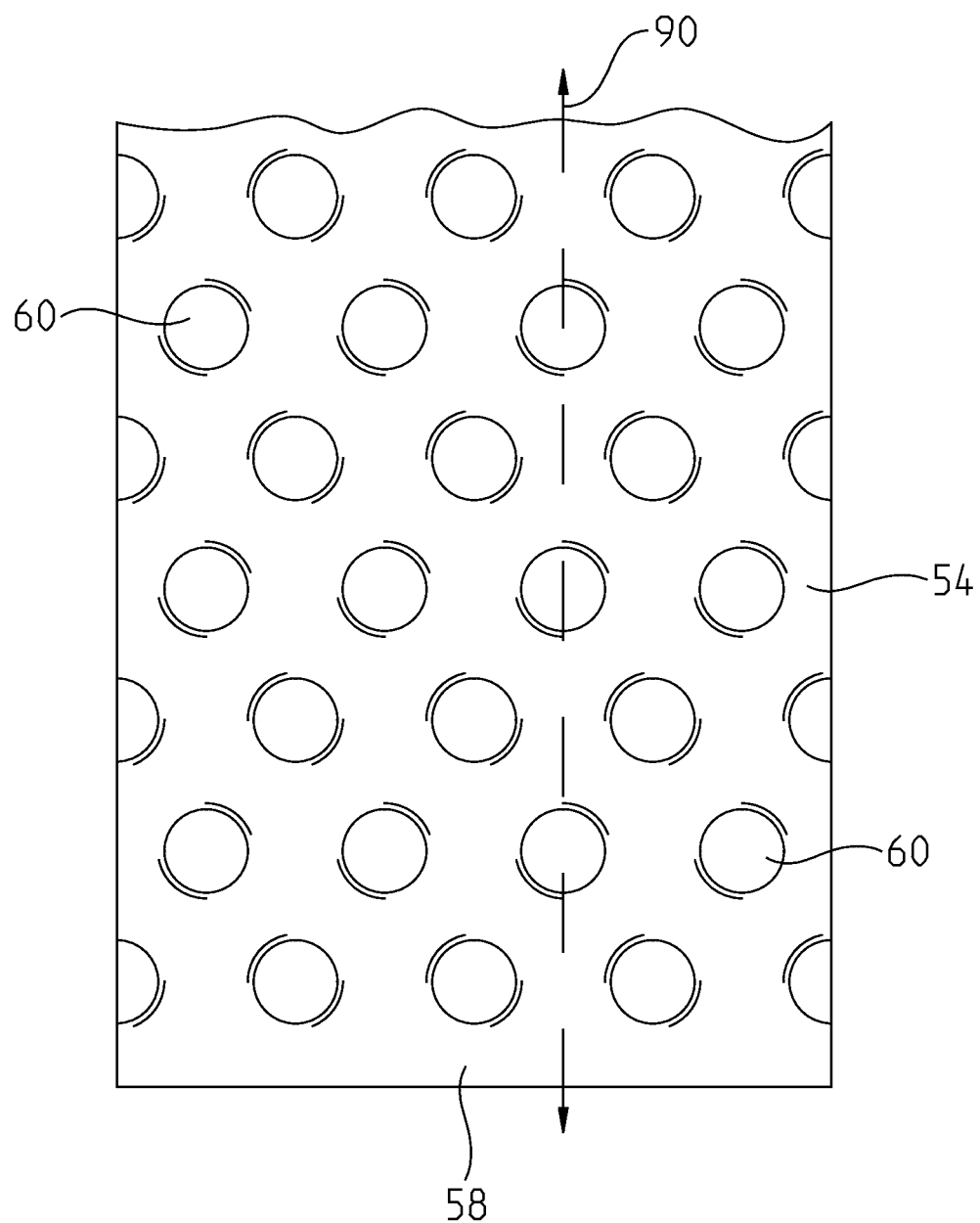
FIG. 10 shows an expanded polar coordinate view of the shaft portion of the impactor device of FIG. 3 with the holes arranged in a staggered matrix.

FIG. 10 shows an expanded polar coordinate view of the shaft portion 54 further displaying the staggered matrix arrangement of the holes. This view shows the shaft portion 54 "unwrapped" along the central axis such that the leftmost position is a zero degree position and the right most position is a three hundred sixty degree position radially relative to the central axis of the shaft. As shown in FIG. 10, the holes 60 are arranged in a staggered matrix such that the holes 60 in one row are offset from the holes in an adjacent row. In the disclosed embodiment, seven rows of holes 60 are provided with four holes in each row. The holes 60 overlap in the axial direction such that a line extending axially along the shaft portion, such as line 90, will intersect one or more of the holes 60. With this arrangement, the holes in each row are situated at ninety degree increments around the shaft, as can be seen from FIGS. 8 and 9. In other words, the center of a hole in a row is ninety degrees removed from the center of an adjacent hole in the row. In the disclosed embodiment, the diameter of each hole is 0.379 inch.

With reference again to FIGS. 3-5, the grip 55 of the impactor device 50 is provided next to the shaft portion 54, toward the first end 56 of the impactor device 50. The grip 55 includes a plurality of fins 72 that extend axially along a length of the shaft surface. The fins 72 are separated by axial indentations 74. The fins 72 and indentations 74 provide a knurled surface that provides an aid in gripping the impaction device 50.

The first end 56 of the bar member 52 provides the impaction surface and is configured to receive a blow from a mallet or other striking device. In the embodiment of FIGS. 3-5, it can be seen that the impaction surface is generally flat. This flat surface helps prevent the surgeon or surgical assistant from hitting the impactor device off axis. FIGS. 6-9 show a similar embodiment to that of FIGS. 3-5, and identical reference numerals are used to identify the same parts. However, in the embodiment of FIGS. 6-9, the impaction surface on the first end 56 of the bar member is convex. In this embodiment, the force of striking tool used by the surgeon is generally concentrated on a smaller area of the impaction surface.

The second end 58 of the bar member is positioned opposite the first end. The second end 58 of the bar member provides a force distributing surface. The force distributing surface is configured to engage an implant member, and thus serves as an implant engagement surface. If the implant member that will be contacted by the implant engagement surface is contoured, the implant engagement surface may be similarly contoured to mate with the surface of the implant member in a congruent fashion. The implant engagement surface shown in FIGS. 3-5 is designed to engage a convex rounded surface, such as the spherical humeral head of a humeral implant. Thus, the implant engagement surface on the second end 58 of the bar member 52 provides a concave rounded surface.

In one embodiment, the impactor device 50 is designed to be somewhere between five and nine inches in length. This length generally facilitates ease of handling by the surgeon along with a sufficient size for many human implant devices. In one embodiment for use with a humeral implant, the impactor device 50 is about seven inches in length. Of course, one of skill in the art will recognize that the impactor device is not limited to a particular length and the impactor device may be designed to any number of different lengths.

The impactor device 50 may be comprised of any of several different materials. Preferably, the material will be moldable, offer high flexural fatigue strength, ridigidity, low wear, toughness and resistance to repeated impact. In one embodiment, the impactor device 50 is comprised of an acetal copolymer such as Celcon®. The simplicity of the impactor device design and use of appropriate material will also allow the impactor device to be easily cleaned through autoclaving.

The impactor device 50 is used by a surgeon or other surgical personnel to assemble a prosthetic device to be implanted in a patient. To this end, the surgeon first chooses an appropriate design and size for the various components of the implant device based on the size and needs of the patient. The implant device comprises a first implant component and a second implant component to be connected by a Morse taper or similar arrangement where the implant components are configured for connection by forcing connection features on the first component into engagement with connection features on the second component.

After selecting appropriate implant components, the surgeon selects an impactor device as set forth above. The impactor device includes a shaft portion, a grip portion, a first end with an impact surface and a second end with an implant engagement surface. A plurality of holes are formed in the axial wall of the shaft portion. The implant engagement surface of the impactor device is configured to engage a surface of the first implant component in a congruent fashion.

Figure 1:
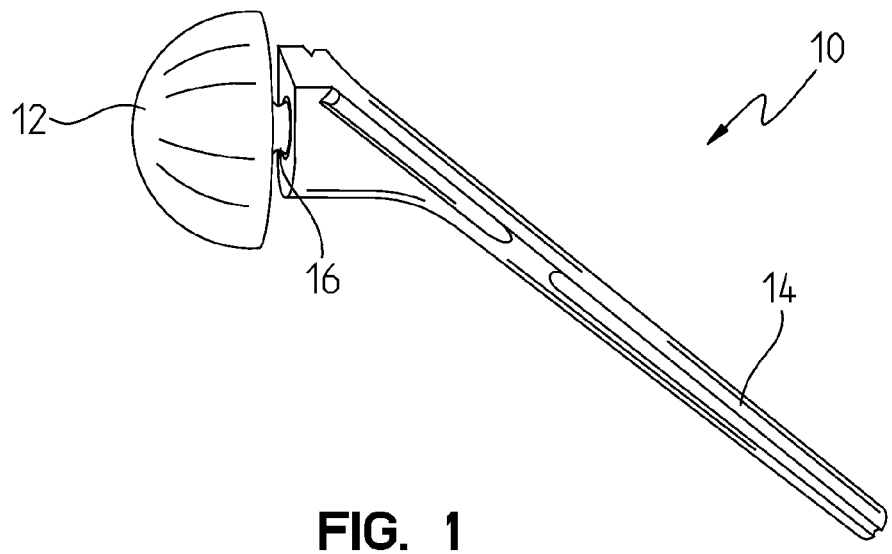
FIG. 1 shows an exemplary prior art humeral implant.
Figure 2:
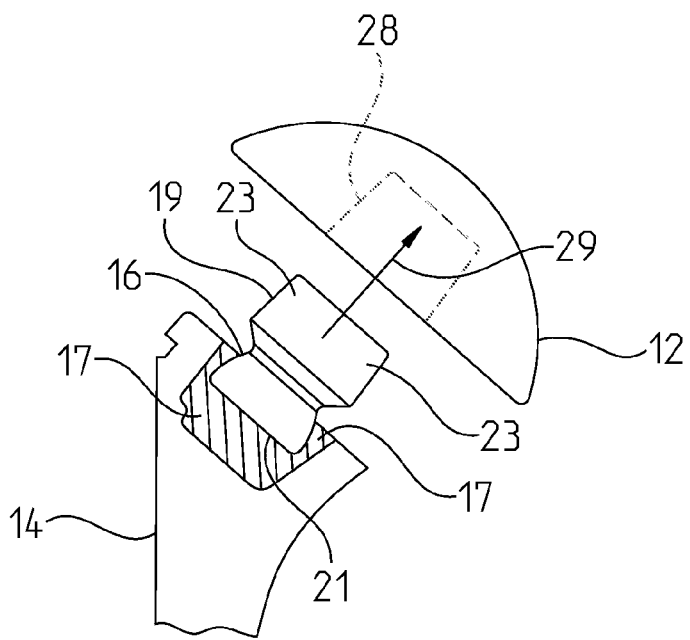
FIG. 2 shows a diagram of the humeral head, humeral stem, and insert for the humeral implant of FIG. 1.

The surgeon aligns the connection features of the first implant component with the connection features of the second an implant component. Next, the surgeon holds the impactor device by the grip portion 55 and brings the implant engagement surface 58 into contact with the first implant component (e.g., the head 12 of the humeral implant of FIGS. 1 and 2). The axis of the impactor device is oriented on the first implant component such that a force transmitted through the impactor device will force the first implant component into full engagement with the second implant component. After properly aligning the impactor device, the surgeon strikes the impaction surface 56 on the impactor device, thus transmitting a force through the impaction device and to the first implant component (e.g., the plug 19 into engagement with the recess 28 in FIG. 2). This force is intended to bring the connection features on the first implant component into engagement with the connection features on the second implant component. The surgeon may be required to strike the impaction surface 56 one or more times to bring the connection features on the first implant component into full engagement with the connection features on the second implant component.

When the surgeon strikes the impactor device, the impactor device dissipates the force transmitted through the bar member and to the implant. In particular, the holes 60 in the impactor device 50 provide voids in the shaft portion 54 so that the shaft portion 54 can compress and expand to dissipate energy. Furthermore, the orientation of the holes 60 not only limits the amount of force that is transmitted down the shaft portion, but also helps to maintain the integrity of the impactor device, such that the impactor device does not fracture, degrade or otherwise fail when struck with a mallet or other striking device.

The staggered matrix orientation and size of the holes on the shaft portion can effectively dissipate about forty percent of the impaction force imparted by a striking device. Thus, even if a five thousand pound force is delivered by a mallet strike, the impactor device 50 will reduce that force to around three thousand pounds, which would be more than enough force to cause the humeral head to engage the humeral insert for most implants. At the same time, the reduced force is much less likely to result in disengagement of or damage to the intermediate components in the implant device.

Although the present invention has been described with respect to certain preferred embodiments, it will be appreciated by those of skill in the art that other implementations and adaptations are possible. For example, the impactor may take the form of different shapes than those shown in the figures, may include different features, may be differently sized, or may be comprised of different materials than those disclosed herein. Moreover, there are advantages to individual advancements described herein that may be obtained without incorporating other aspects described above. Therefore, the spirit and scope of the appended claims should not be limited to the description of the preferred embodiments contained herein.

What is claimed is:

1. An impactor device configured to impact an implant member, the impactor device comprising:
 a bar member including a hollow shaft with an outer shaft surface, an inner shaft surface, a first end, and a second end, the first end including an impaction surface configured to receive a blow from a striking device and the second end including an implant engagement surface configured to engage the implant member; and
 a plurality of holes provided in the shaft and extending from the outer shaft surface to the inner shaft surface, wherein the plurality of holes are arranged such that when the hollow shaft is viewed in an unwrapped view, any straight line passing axially along the outer shaft surface intersects at least one of the plurality of holes.

2. The impactor device of claim 1 wherein the outer shaft surface is cylindrical in shape.

3. The impactor device of claim 1 wherein the implant engagement surface is contoured to mate with a surface of the implant member.

4. The impactor device of claim 3 wherein the implant engagement surface is rounded and concave and the surface of the implant member is rounded and convex.

5. The impactor device of claim 1 wherein the bar member is between five and nine inches in length.

6. The impactor device of claim 5 wherein the bar member is about seven inches in length.

7. The impactor device of claim 1 wherein the plurality of holes are arranged in a staggered matrix around the hollow shaft.

8. The impactor device of claim 1 wherein the plurality of holes are arranged in a plurality of rows around the hollow shaft.

9. The impactor device of claim 8 wherein each row of the plurality of rows comprises four holes, and wherein each hole in each row is displaced through 90° around a longitudinal axis of the hollow shaft relative to an adjacent hole in the row.

10. An impactor device configured to deliver an impact force, the impactor device comprising:

a hollow shaft including a plurality of perforations extending from an outer surface of the hollow shaft to an inner surface of the hollow shaft, wherein the plurality of perforations are arranged such that when the hollow shaft is viewed in an unwrapped view, any straight line passing axially along the outer shaft surface intersects at least one of the plurality of perforations;

an impaction surface located on one end of the hollow shaft and configured to receive a blow from a striking device; and a force distributing surface on the opposite end of the hollow shaft.

11. The impactor device of claim 10 wherein the plurality of perforations are arranged in a pattern.

12. The impactor device of claim 11 wherein the plurality of perforations are arranged in a staggered matrix.

13. The impactor device of claim 10 wherein the force distributing surface comprises an implant engagement surface which is contoured to mate with a component of an implant.

14. The impactor device of claim 13 wherein the implant engagement surface is rounded and concave and the surface of the implant member is rounded and convex.

15. The impactor device of claim 10 wherein the plurality of perforations are arranged in a plurality of rows around the hollow shaft.

16. The impactor device of claim 15 wherein each row of the plurality of rows comprises four perforations, and wherein each perforation in each row is displaced through 90° around a longitudinal axis of the hollow shaft relative to an adjacent perforations in the row.

* * * * *